(12) United States Patent
Yen (10) Patent No.: US 6,810,752 B1
(45) Date of Patent: Nov. 2, 2004

(54) BLOCK TEST STAND

(76) Inventor: Jia-Yih Yen, F1, No.7, Alley 2, Industry Area 1 Rd., Taichung City (TW)

( * ) Notice: Subject to any disclaimer, the term of this patent is extended or adjusted under 35 U.S.C. 154(b) by 0 days.

(21) Appl. No.: 10/830,838

(22) Filed: Apr. 23, 2004

(51) Int. Cl.[7] ................................................. G01L 1/00
(52) U.S. Cl. .............................. 73/855; 73/856; 73/161; 174/250
(58) Field of Search .............................. 73/37–38, 161, 73/855–861; 174/250

(56) References Cited

U.S. PATENT DOCUMENTS

| | | | | |
|---|---|---|---|---|
| 3,752,626 A | * | 8/1973 | Trautner et al. | 425/262 |
| 5,313,841 A | * | 5/1994 | Layher | 73/827 |
| 5,339,515 A | * | 8/1994 | Brackett et al. | 73/161 |
| 6,305,230 B1 | * | 10/2001 | Kasukabe et al. | 73/855 |
| 6,655,192 B2 | * | 12/2003 | Chavdar | 73/38 |

* cited by examiner

*Primary Examiner*—Edward Lefkowitz
*Assistant Examiner*—Alandra Ellington
(74) *Attorney, Agent, or Firm*—Alan Kamrath; Nikolai & Mersereau, P.A.

(57) ABSTRACT

A block test stand includes a body having a base and two rods each having a first end secured on the base and a second end having a barrel laterally secured on the two rods. A bearing member is partially slidably received in the barrel. The bearing member includes a piston cap slidably received in the barrel, and a piston is received in the piston cap and extends through the barrel. A connector is secured on a distal end of the piston. A bearing seat is connected to the connector. The bearing seat includes a block and a spheroid secured on the block. The spheroid is partially universally received in the socket in the connector and a concentric ring is sleeved on the connector and secured on the block to hold the block in place.

7 Claims, 8 Drawing Sheets

BLOCK TEST STAND

BACKGROUND OF THE INVENTION

1. Field of the Invention

The present invention relates to a block test stand, and more particularly to a block test stand for testing a compressive strength of a cylindrical concrete specimens.

2. Description of Related Art

Figure 6:
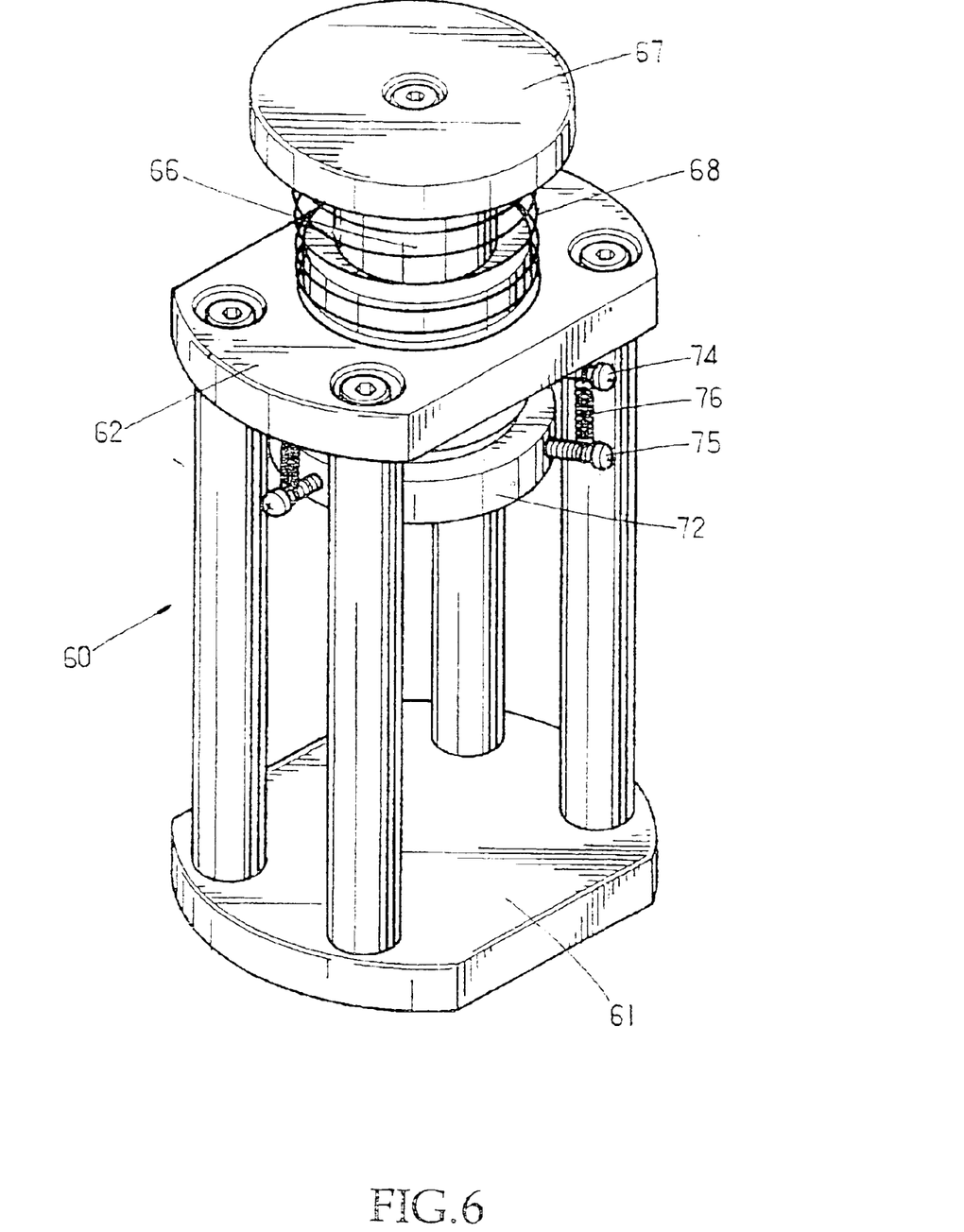
FIG. 6 is a perspective view of a conventional block test stand in accordance with the present invention.
Figure 7:
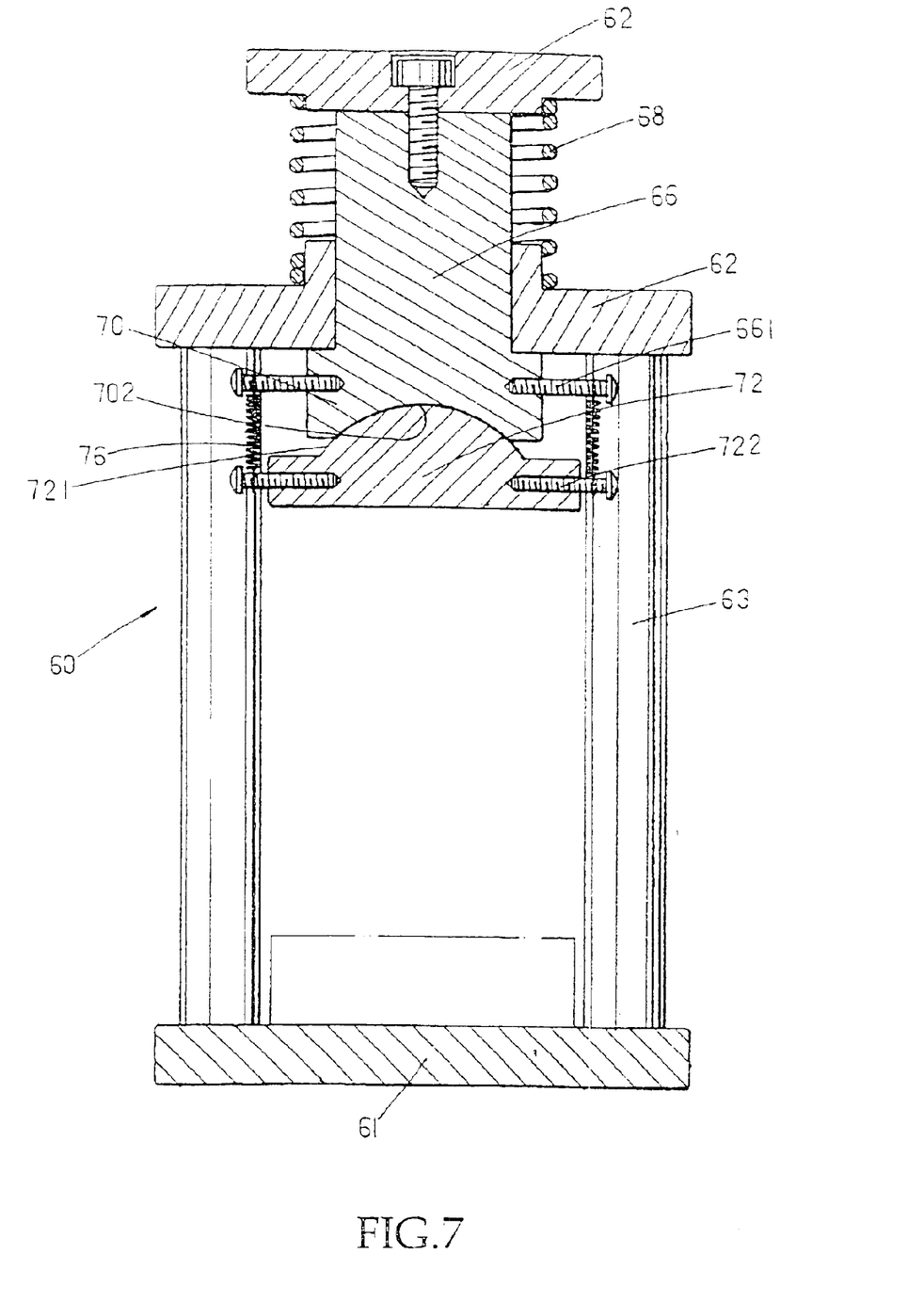
FIG. 7 is a cross-sectional view of the conventional block test stand in FIG. 6.
Figure 8:
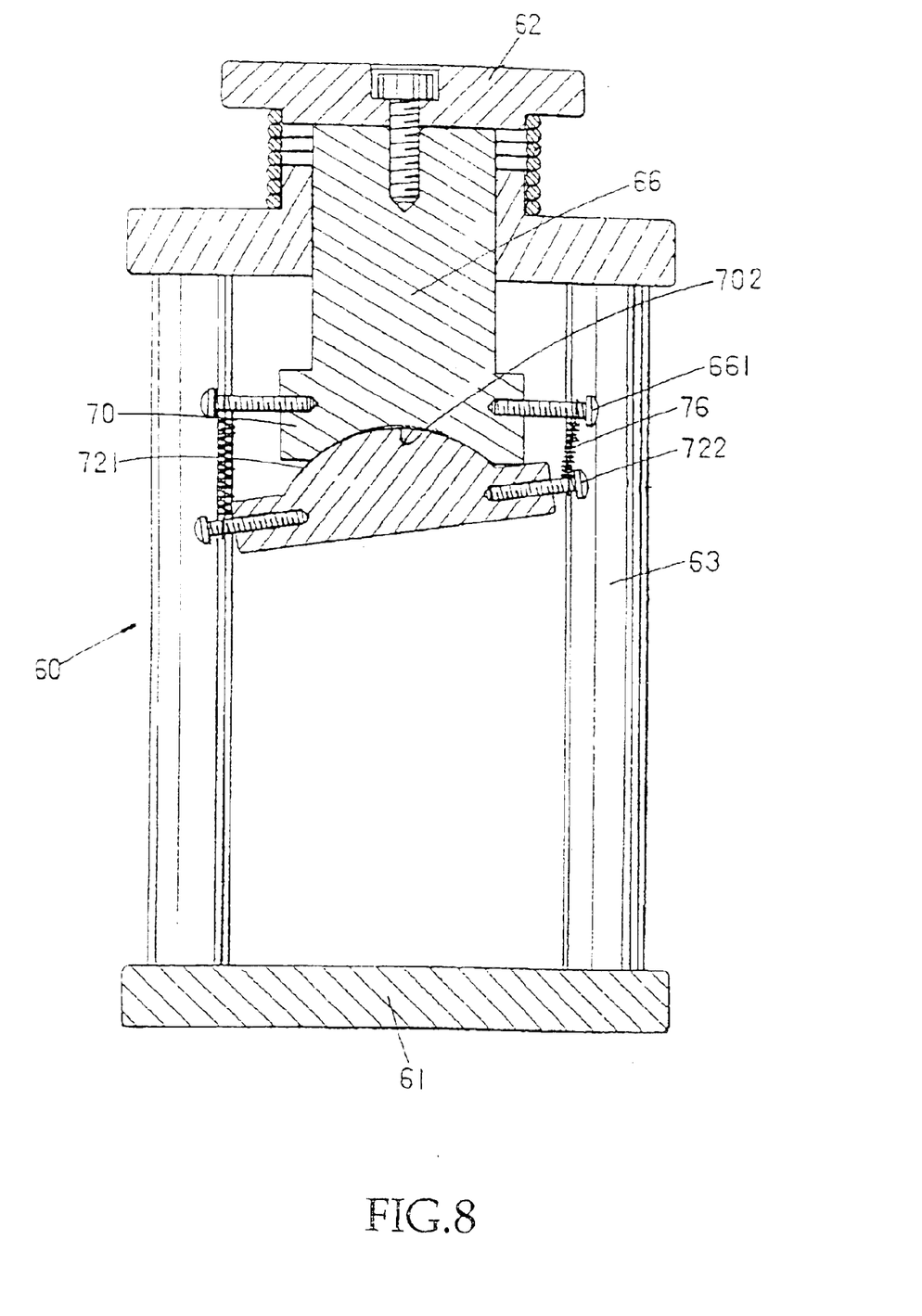
FIG. 8 is a side operational view in cross-section of the conventional block test stand in FIG. 6.

A conventional block test stand (60) in accordance with the prior art shown in FIGS. 6–8 comprises a base (61), four interconnecting rods (63) each having a first end secured on the base (61) and a upper plate (62) secured on a second end of each of the four interconnecting rods (63). A bearing block (66) centrally longitudinally extends through the upper plate (62). The bearing block (66) includes a first end having a bearing plate (67) mounted thereon and a second end having a curved indentation (702) defined therein. A first spring (68) is compressively sleeved on the bearing block (66) between the bearing plate (67) and the upper plate (62). A seat (72) is universally connected to the second end of the bearing block (66). The seat (72) includes a spherical protrusion (721) extending therefrom and partially universally received in the curved indentation (702) in the second end of the bearing block (66). The bearing block (66) includes first stubs (661) laterally extending from an outer periphery thereof and the seat (72) includes multiple second stubs (722) laterally extending from an outer periphery of the seat (72). Each second stub (722) linearly aligns with a corresponding one of the multiple first stubs (661) of the bearing block (66). A second spring (76) is mounted between a first stub (661) and a second stub (722) that align with each other for making the seat (72) abut the second end of the bearing block (66). The cylindrical concrete specimen (not numbered) is situated within the four interconnecting rods (63), and between the base (61) and the upper plate (62) during testing compressive strength.

However, the conventional block test stand in accordance with the prior art includes several disadvantages as follow:

1. The four interconnecting rods (63) limit the size of the concrete specimen. The concrete specimen is not easily to be situated within the four interconnecting rods (63) and taken out after being tested.

2. The only support for holding between the seat (723) and the bearding block (66) depends solely on the second springs (76). Consequently, the conventional block test stand (60) will not be operated when any one of the multiple second springs (76) is broken.

3. Instead of hidden inside a protected cover, the first spring (68) is exposed and unprotected. Therefore, the first spring (68) is prone top erosion and broken.

4. The user has no choice but replacing the seat (72) and the bearing block (66) when an abrasion happened on the seat (72) and the bearing block (66) because they are not a one-piece assembly.

The present invention has arisen to mitigate and/or obviate the disadvantages of the conventional block test stand.

SUMMARY OF THE INVENTION

The main objective of the present invention is to provide an improved block test stand for testing specimen that is easily to be operated and has a longer lifetime.

To achieve the objective, the block test stand in accordance with the present invention comprises a body having a base and two rods each having a first end secured on the base and a second end having a barrel laterally secured on the two rods. A bearing member is partially slidably received in the barrel. The bearing member includes a piston cap slidably received in the barrel, and a piston is received in the piston cap and extends through the barrel. A connector is secured on a distal end of the piston. A bearing seat is connected to the connector. The bearing seat includes a block and a spheroid secured on the block. The spheroid is partially universally received in the socket in the connector and a concentric ring is sleeved on the connector and secured on the block to hold the block in place.

Further benefits and advantages of the present invention will become apparent after a careful reading of the detailed description with appropriate reference to the accompanying drawings.

DETAILED DESCRIPTION OF THE INVENTION

Referring to the drawings and initially to FIGS. 1–4, a block test stand in accordance with the present invention comprises a body (1), a bearing member (2) secured on a top of the body (1) and a bearing seat (3) longitudinally mounted to the bearing member (2).

Figure 1:
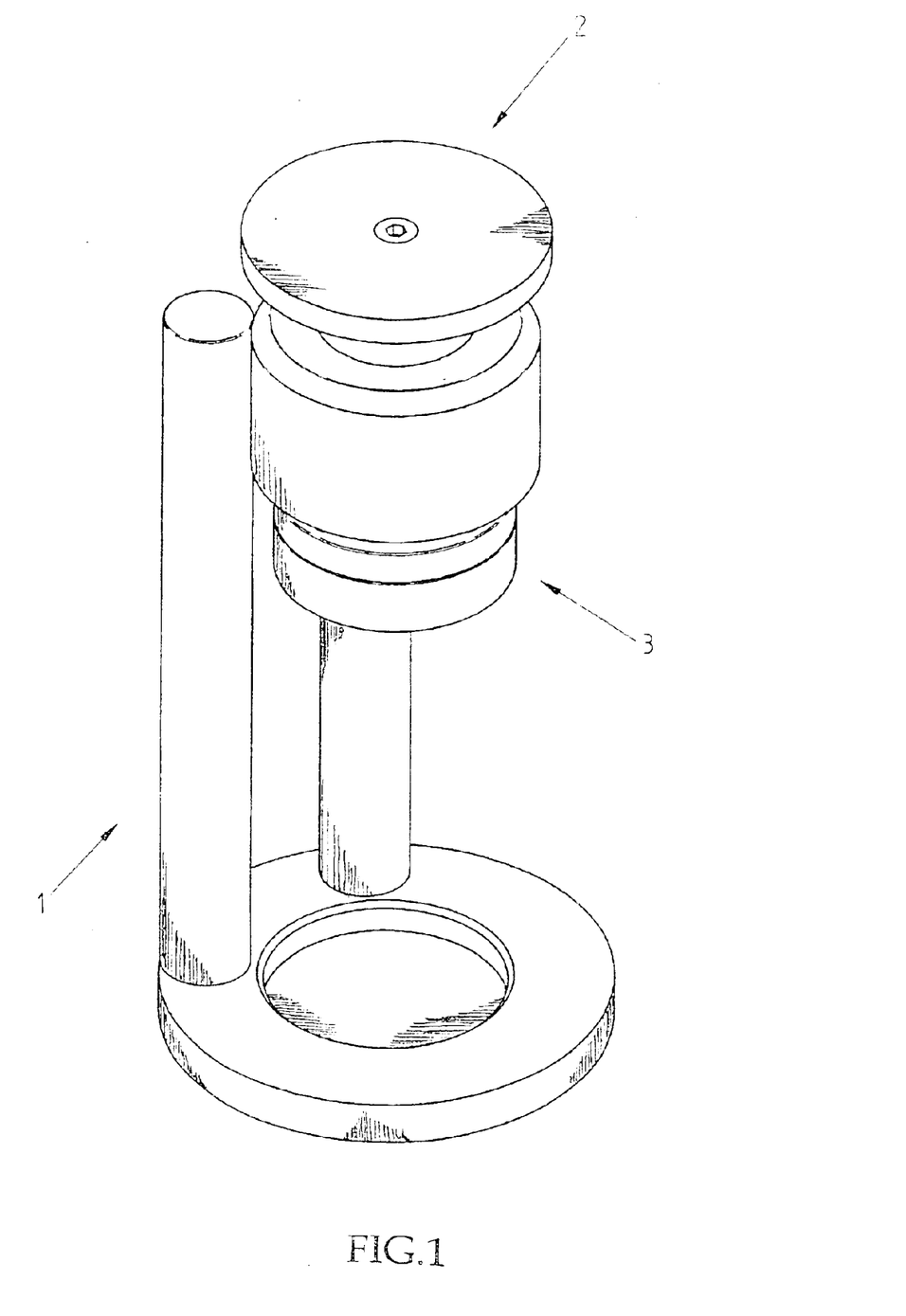
FIG. 1 is a perspective view of a block test stand in accordance with the present invention.
Figure 2:
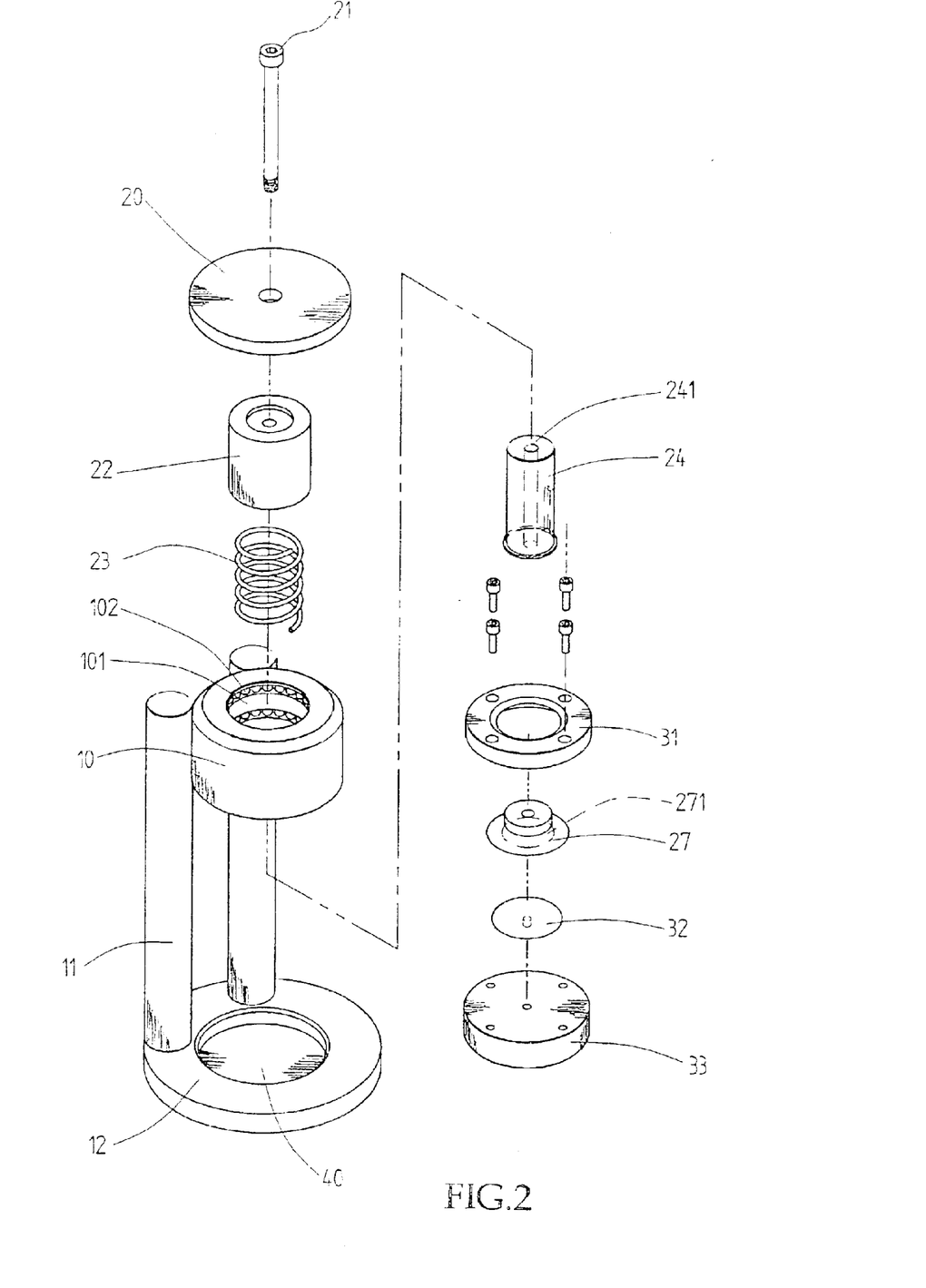
FIG. 2 is an exploded perspective view of the block test stand in FIG. 1.
Figure 3:
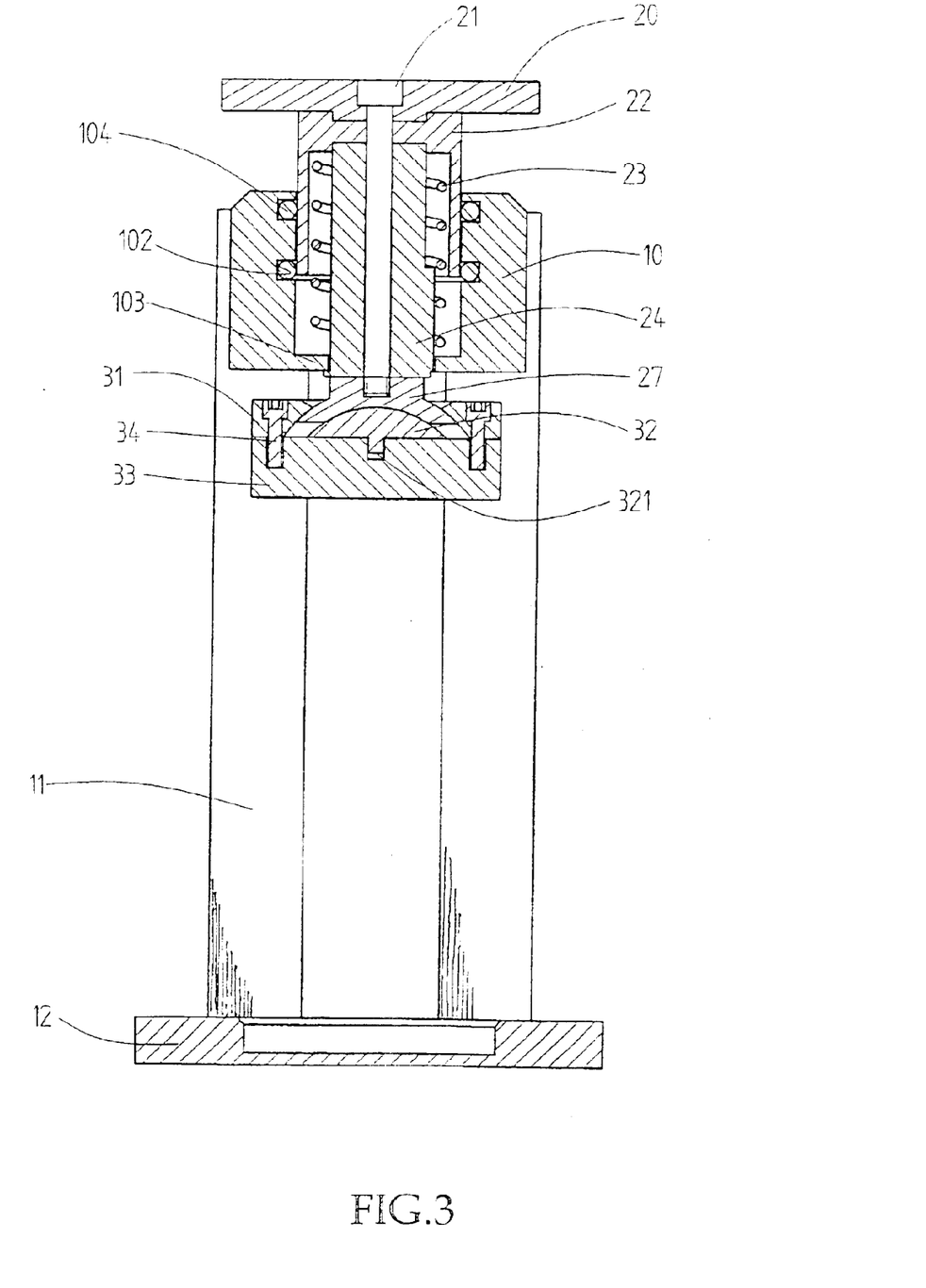
FIG. 3 is a cross-sectional view of the block test stand in FIG. 1.
Figure 4:
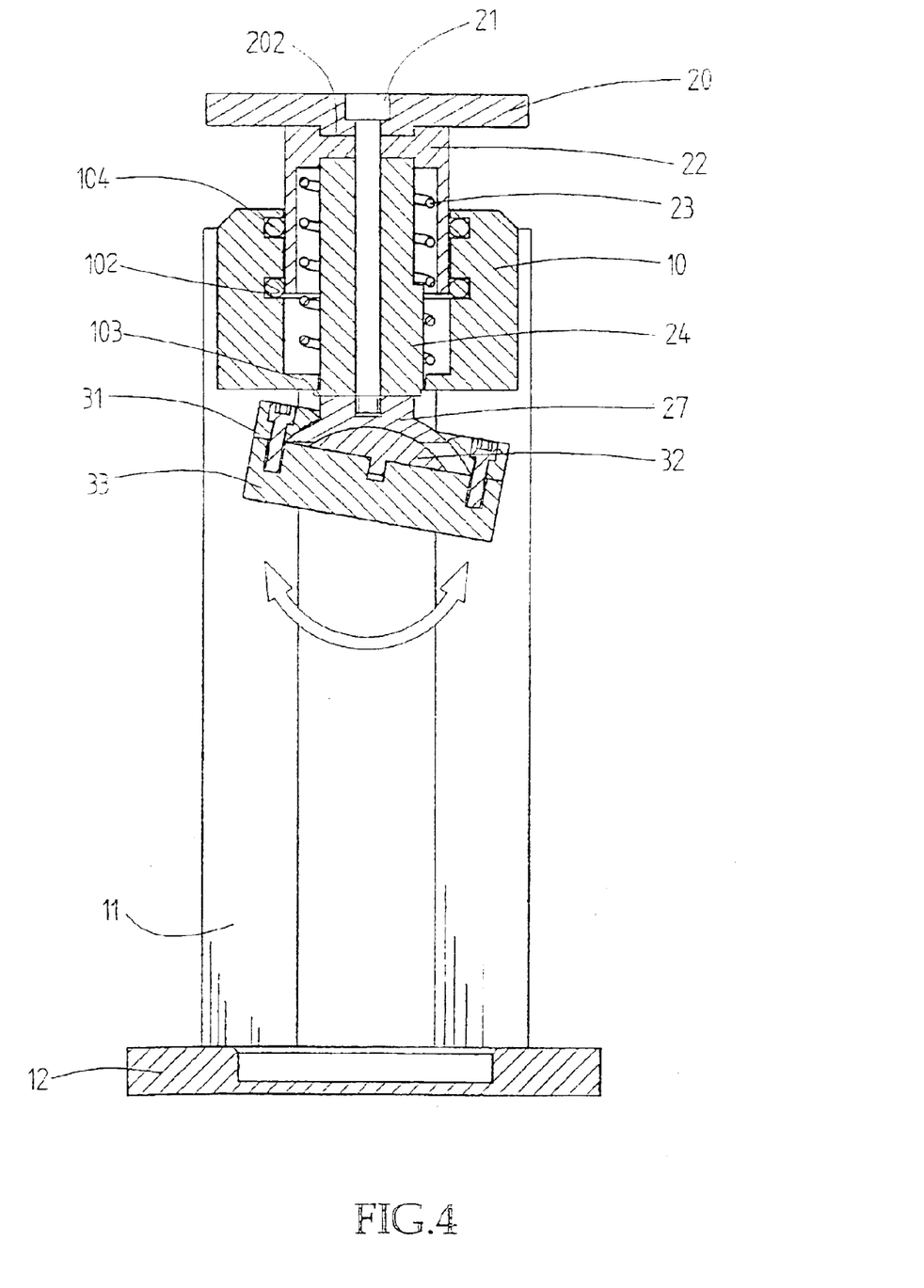
FIG. 4 is an operational side plan view in cross-section of the block test stand of the present invention.
Figure 5:
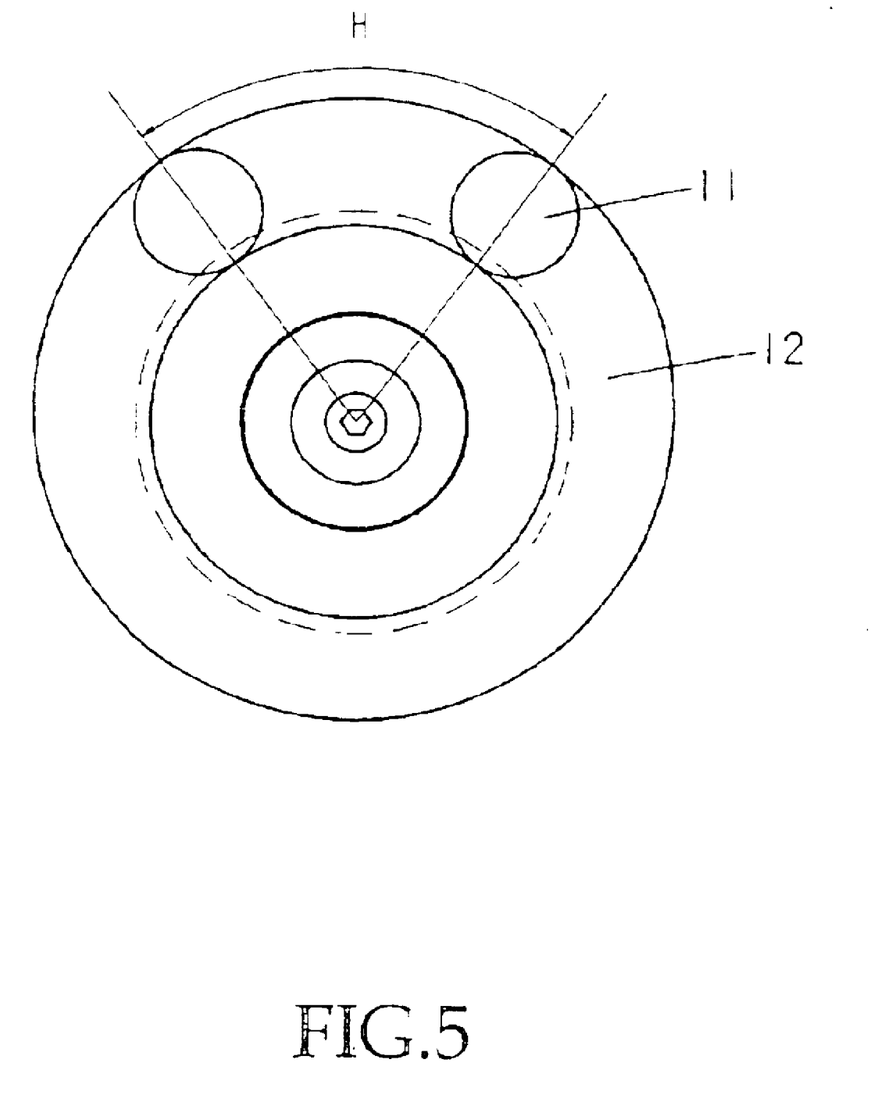
FIG. 5 is a top plan view of the block test stand in FIG. 1 for showing an angle between the two rods of the present invention.

The body (1) includes a base (12) and two rods (11) longitudinally mounted to the base (12). Further with reference to FIG. 5, an angle (H) is formed between the two rods (11) relative to a center of the bearing member (2). In the preferred embodiment of the present invention, the angle (H) is set about 70 degrees. Each rod (11) has a first end secured on the base (12) and a second end having a barrel (10) laterally mounted to the two rods (11). The barrel (10) has a through hole (101) centrally defined therein and an annular lip (103) inwardly extending from an inner periphery of the through hole (101) near a bottom of the barrel (10). At least annular groove (102) is defined in the inner periphery on the through hole (101) and fully filled with steel balls (104).

The bearing member (2) includes a piston cap (22) slidably received in the through hole (101) in the barrel (10) and the steel balls (104) in the at least one annular groove (102) can reduce the friction between the barrel (10) and the piston (22). The piston cap (22) is hollow and a piston (24) is centrally received in the piston cap (22). The piston (24) downward extends through the barrel (10). A bearing plate (20) is mounted on a top of the piston cap (22) and a connector (27) is mounted to a bottom of the piston (24). A bolt (21) extends through the bearing plate (20), the piston cap (22) and the piston (24), and is screwed onto the connector (27) to securely connect the bearing plate (20), the piston cap (22), the piston (24) and the connector (27). The connector (27) has a socket (271) defined in a bottom thereof and the connector (27) has an outer periphery concentrically corresponding to that of the curved indentation (271) in the connector (27).

The bearing seat (3) includes a block (33) having a spheroid (32) centrally secured on the block (33) and partially received in the socket (271) in the connector (27). The spheroid (32) has a curvature being equal to that of the socket (271) so that the block (33) can be universally moved relative to the connector (27). A concentric ring (31) is concentrically sleeved on the connector (27) and secured on the block (33) to hold the block (33) in place. The concentric ring (31) has a curved inner surface corresponding to the connector (27). The cylindrical concrete specimen (not numbered) is situated under the bearing seat (3) during testing compressive strength.

As described above, the block test stand in accordance with the present invention has several advantages as follow.

1. The two rods (11) are located at an angle about 70 degrees that leaves the body (1) with a wide-open space so that the block test stand of the present invention can receive a great specimen and more easily put in or take out the tested specimen.

2. The spring (23) is received din the piston cap (22) so that the piston cap (22) provides a protection to the spring (23) and the spring (23) has a longer lifetime than that of the conventional block test stand.

3. The annular groove (102) in the inner periphery of the through hole (101) and the steel balls received in the annular groove (102) can effectively reduce the friction force between the barrel (10) and the piston cap (22).

Although the invention has been explained in relation to its preferred embodiment, it is to be understood that many other possible modifications and variations can be made without departing from the spirit and scope of the invention as hereinafter claimed.

What is claimed is:

1. A block test stand comprising:

a body including a base and two rods each having a first end secured on the base and a second end having a barrel laterally secured on the two rods, the barrel having a through hole centrally defined therein and an annular lip inwardly extending from an inner periphery of the through hole near a bottom of the barrel;

a bearing member partially slidably received in the barrel, the bearing member including a piston cap slidably received in through hole in the barrel, and a piston received in the piston cap and extending through the barrel, a spring sleeved on the piston and abutting the annular lip and the piston cap, a connector secured on a distal end of the piston and a bearing plate secured on a top of the piston cap, the connector having a socket defined in a bottom thereof; and a bearing seat connected to the connector, the bearing seat including a block and a spheroid secured on the block, the spheroid partially universally received in the socket in the connector, a concentric ring sleeved on the connector and secured on the block to hold the block in place.

2. The block test stand as claimed in claim 1, wherein an angle is formed between the two rods relative to a center of the bearing member and set about 70 degrees.

3. The block test stand as claimed in claim 1, wherein the barrel includes at least one annular groove defined in the inner periphery of the through hole in the barrel and fully filled with steel balls for deducing a friction force between the piston cap and the barrel.

4. The block test stand as claimed in claim 1, wherein the concentric ring has a curved inner surface corresponding to the connector.

5. The block test stand as claimed in claim 2, wherein the barrel includes at least one annular groove defined in the inner periphery of the through hole in the barrel and fully filled with steel balls for deducing a friction force between the piston cap and the barrel.

6. The block test stand as claimed in claim 2, wherein the concentric ring has a curved inner surface corresponding to the connector.

7. The block test stand as claimed in claim 3, wherein the concentric ring has a curved inner surface corresponding to the connector.

* * * * *